United States Patent [19]

Rosenfeld et al.

[11] Patent Number: 5,177,181
[45] Date of Patent: Jan. 5, 1993

[54] DIAMINES AND PHOTOSENSITIVE POLYIMIDES MADE THEREFROM

[75] Inventors: Jerold Rosenfeld, Tonawanda; Jin-O Choi; David Y. Tang, both of Amherst; John Tyrell, Williamsville, all of N.Y.

[73] Assignee: Occidental Chemical Corporation, Niagara Falls, N.Y.

[21] Appl. No.: 710,872

[22] Filed: Jun. 6, 1991

[51] Int. Cl.$^5$ .............................................. C08G 69/26
[52] U.S. Cl. .................. 528/353; 528/125; 528/126; 528/179; 528/188; 528/223; 528/229; 528/337; 528/348; 528/351; 528/373
[58] Field of Search ............... 528/336, 125, 126, 179, 528/188, 223, 229, 337, 348, 351, 353, 373

[56] References Cited

U.S. PATENT DOCUMENTS

| | | | |
|---|---|---|---|
| 4,321,319 | 3/1982 | Shoji | 528/185 |
| 4,451,551 | 5/1984 | Kataoka | 430/270 |
| 4,586,997 | 5/1986 | Lee | 525/426 |
| 4,619,500 | 10/1986 | Ahne | 525/426 |
| 4,741,988 | 5/1988 | Van der Zande | 430/312 |
| 4,754,016 | 6/1988 | Ai et al. | 528/336 |
| 4,782,009 | 11/1988 | Bolon | 430/326 |
| 4,829,131 | 5/1989 | Lee | 525/426 |
| 5,025,088 | 6/1991 | Maeda et al. | 528/353 |

FOREIGN PATENT DOCUMENTS

| | | |
|---|---|---|
| 3107519 | 9/1982 | Fed. Rep. of Germany . |
| 59-108751 | 6/1984 | Japan . |
| 59-232122 | 12/1984 | Japan . |

OTHER PUBLICATIONS

An article by Hurng-Rern Lee et al., *Journal of Polymer Science: Part A: Polymer Chemistry*, vol. 27, 1481–1497 (1989) "Synthesis, Characterization, and Kinetics Studies of Organic Soluble Photosensitive Copolyimide".
Chemical Abstract Registry No. compounds RN 93576-86-4, RN 84875-45-6, RN 84874-28-2, RN 81386-02-5.

*Primary Examiner*—John Kight, III
*Assistant Examiner*—Shelley Wright
*Attorney, Agent, or Firm*—Wayne A. Jones; Richard D. Fuerle

[57] ABSTRACT

Disclosed is an aromatic diamine having the general formula

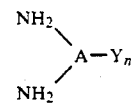

where A is a group containing at least one aromatic ring, each Y is independently selected from

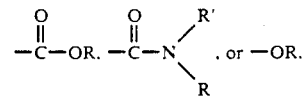

R is a group containing at least one olefinically unsaturated group, R' is hydrogen, alkyl to $C_{25}$, aryl, or R, n is 1 to 4, and the number of olefinic groups in Y is at least 3 when each Y is

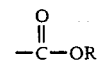

and otherwise is at least 2. Photosensitive polyamic acids and polyimides can be prepared from the aromatic diamines which can be crosslinked with light to a mask to form patterns on a substrate.

26 Claims, 1 Drawing Sheet

FIG. 1
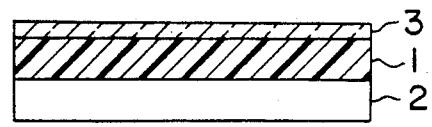
FIG. 2
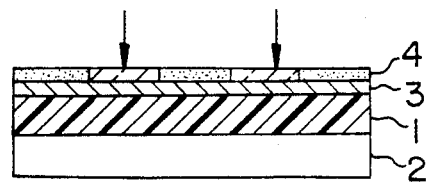
FIG. 3
FIG. 4
FIG. 5
FIG. 6
FIG. 7
FIG. 8
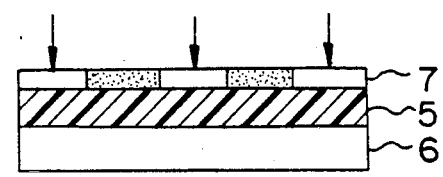
FIG. 9
FIG. 10
FIG. 11

DIAMINES AND PHOTOSENSITIVE
POLYIMIDES MADE THEREFROM

BACKGROUND OF THE INVENTION

This invention relates to novel aromatic diamines containing olefinic groups and to photo-crosslinkable polyamic acids and polyimides made therefrom. In particular, it relates to aromatic diamines having pendant groups that contain at least two olefinic groups, and to soluble polyimides made therefrom for use in semiconductor fabrication.

Polyimides are used in the semiconductor industry as dielectric coatings on silicon chips. There are several processes by which polyimide coatings can be deposited on silicon chips. The conventional process is a multistep process that employs a photoresist to mask the etching of a polyamic acid layer. The conventional process is illustrated in the drawing which will be hereinafter described.

A second process is described in U.S. Pat. No. 4,321,319. In the process of that patent, a solution of a photosensitive polyamic acid is formed from a dianhydride and a diamine that contains a photosensitive group. The solution, with a sensitizer present, is spread on a substrate and the solvent is evaporated to form a soluble polyamic acid coating. The coating is exposed to light through a mask which crosslinks the exposed portions of the coating, rendering them insoluble. The unexposed portions are then dissolved in a solvent and removed and the exposed portions are heated to close the imide ring and harden the film. This method must be used to form a pattern if the polyimide is insoluble and therefore a coating cannot be formed from a solution of the polyimide. This is a useful method, but when the imide ring is closed water is condensed out and its removal can leave voids, pinholes, or blisters in the coating.

SUMMARY OF THE INVENTION

We have discovered certain aromatic diamines that are very useful in making photosensitive polyamic acids and photosensitive polyimides. Unlike prior diamines used in making photosensitive polyamic acids and polyimides, the diamines of this invention contain pendant groups that contain multiple olefinic crosslinking groups. Because of these multiple olefinic groups, the diamines of this invention are more highly crosslinkable than prior diamines, which results in a more densely crosslinked polymer and a higher resolution pattern. While a person skilled in the art might expect that the presence of multiple olefinic groups on a single pendant chain may lead to intramolecular crosslinking rather than intermolecular crosslinking, we have found that crosslinking on the same molecule can be avoided by careful preparation of the diamines, and that the diamines are stable.

We have also found that by carefully selecting the dianhydride (or mixtures or dianhydrides) used to form the polyimide, as well as by the use of siloxane-containing diamines and by the length of the siloxane groups on those diamines, we can obtain photosensitive polyimides that are soluble. As a result, unlike the process disclosed in U.S. Pat. No. 4,321,319, we can form a coating on a substrate from a solution of our photosensitive polyimides. The solvent in the solution can be evaporated and portions of the polyimide coating can be crosslinked with light to form an insoluble pattern. The unexposed soluble portions of the polyimide can then be dissolved in a solvent or combination of solvents. Because the polyimide is already formed no water of condensation is formed in the coating when the imide ring is closed, and blisters, pinholes, and voids produced by the evaporation of water of condensation are avoided.

Finally, as will become clear in the discussion of the accompanying drawing, because the polyimide and polyamic acids of this invention are themselves photosensitive, it is no longer necessary to use a photoresist coating to form a mask for etching the polyimide coating, as it was in the conventional process. And, because the polyimide is stable and has favorable electrical properties, it can remain as a permanent part of the electrical device. As a result, a number of steps in the conventional process are eliminated. In addition, the crosslinking of the polyimides by light produces a sharper edge to the pattern than the edge produced by etching or dissolving away the polyimide in the conventional process, and a sharper edge means a higher resolution pattern. Other advantages of the materials and process of this invention will no doubt become apparent to those skilled in the art.

BRIEF DESCRIPTION OF THE DRAWING

The accompanying drawing is a diagram comparing the conventional process of making a pattern in a polyimide coating on a substrate with the process of this invention for making a pattern in a polyimide coating on a substrate. FIGS. 1 to 7 refer to the conventional process while FIGS. 8 to 11 refer to a certain presently preferred embodiment of a process according to this invention.

DESCRIPTION OF THE INVENTION

In the drawing, in FIG. 1, a coating of a soluble polyamic acid 1 that is not photo-crosslinkable has been formed on a substrate 2 which can be, for example, a silicon chip. In FIG. 2, a layer of an insoluble photoresist 3 has been formed on polyamic acid layer 1. In FIG. 3, a mask 4 has been placed over photoresist layer 3. (The pattern can also be projected onto the photoresist.) The mask has been exposed to light in a direction perpendicular to the mask, resulting in the breakdown of those portions of the photoresist that are exposed to the light, so that they are rendered soluble. (The light could also insolublize a soluble photoresist.) In FIG. 4, the mask 4 has been removed and those portions of photoresist 3 that were exposed to light and rendered soluble have been washed away with a solvent, leaving a pattern in the photoresist. In FIG. 5, the patterned photoresist 3 is used as a mask so that exposed portions of polyamic acid layer 1 can be removed by etching or dissolution in a solvent, leaving an identical pattern in polyamic acid layer 1. In FIG. 6, photoresist 3 is removed and in FIG. 7 the polyamic acid remaining is imidized.

Not only does this process involve many steps, but some of the steps are difficult to perform. For example, in FIG. 6 a solvent must be used that dissolves the photoresist, but does not dissolve the polyamic acid. In FIG. 7 water of condensation and residual solvent must be removed without damaging the polyimide layer or the substrate.

Referring now to the process of this invention, in FIG. 8 a soluble photosensitive polyimide coating 5 according to this invention has been formed on substrate 6. In FIG. 9, a mask 6 is placed over polyimide coating 5 (or the pattern is projected onto coating 5) and mask 6 is exposed to light coming from a perpendicular direction. The light that passes through the mask and strikes polyimide layer 5 crosslinks and insolublizes the exposed portions of the polyimide. In FIG. 10, the unexposed and soluble portions of the polyimide have been dissolved in a solvent and removed. Finally, in FIG. 11, the polyimide is cured (i.e., residual solvent is evaporated). (Alternatively, coating 5 can be a polyamic acid which is imidized in FIG. 11.)

As will be apparent by comparing the conventional process with the process of this invention, the process of this invention involves fewer steps and eliminates the need for a photoresist layer. In addition, while the conventional process relies upon etching or dissolution of the polyamic acid layer through a mask to form a pattern in it, the process of this invention relies upon crosslinking of a polyimide (or polyamic acid) layer to form the pattern. The etching or dissolving step in the conventional process is more likely to result in jagged or undercut edges than is the crosslinking that occurs in the process of this invention. Therefore, the process of this invention can produce a higher resolution pattern which has the advantages of greater reliability and greater circuit density.

The Crosslinkable Diamines

The crosslinkable aromatic diamines of this invention have the general formula

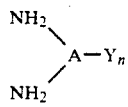

where A is a group containing at least one aromatic ring, Y is

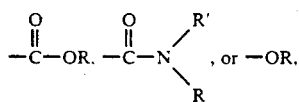

R is a group containing at least one olefinically unsaturated group, R' is hydrogen, alkyl to $C_{25}$, aryl, or R, n is 1 to 4, and the number of olefinic groups in each Y is at least 3 when each Y is

and otherwise is at least 2.

Examples of various aromatic ring-containing groups that can be used as A in the formula include

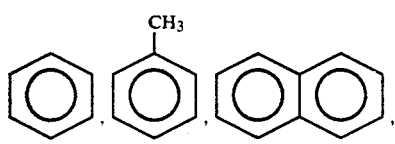

The preferred aromatic group is phenyl, because those diamines are easier to prepare. The 3,5-diamino phenyl compounds are preferred for the same reason.

The Y group is preferably an ester or an amide group and the R group is preferably a pentaerythritol-containing group. Examples of suitable pentaerythritol R groups include triallyl pentaerythritol, pentaerythrityl trimethacrylate, pentaerythrityl triacrylate, dipentaerythrityl pentaacrylate, and dipentaerythrityl pentamethacrylate. In the diamines of this invention, there must be at least two pendant olefinic groups on each diamine, except that when each Y is

there must be at least 3. The preferred crosslinkable aromatic diamines are triallylpentaerythrityl 3,5-diaminobenzoate (TAP)

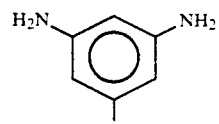

pentaerythrityl trimethacrylate 3,5-diaminobenzoate (PETM)

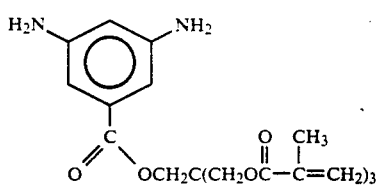

pentaerythrityl triacrylate 3,5-diaminobenzoate (PETA)

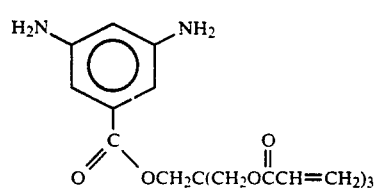

and N,N-diallyl 3,5-diaminobenzamide (DAA)

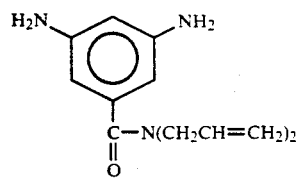

because the materials required for their preparation are readily available and they produce polyimides having good properties.

Preparation of Crosslinkable Diamines

The aromatic crosslinkable diamines of this invention can be prepared, for example, by reacting the corresponding dinitro acid chloride with an unsaturated alcohol (if an ester linkage is desired) or with an unsaturated amine (if an amide linkage is desired). The two nitro groups are then reduced to amine groups by, for example, reacting one mole of the dinitro compound with about 10 moles of metallic iron powder and about 10 moles of acetic acid. Both reactions occur at 25° C. and can be followed by chromatography. Diamines where Y has an ether linkage can be prepared by, for example, reacting the corresponding dinitrochloro compound with an alcohol and a base to form the dinitro ether, then reducing to the diamine. Details of the preparations of some of these diamines are given in the examples that follow.

Preparation of Polyamic Acids

Photosensitive polyamic acids can be prepared using the crosslinkable aromatic diamines of this invention. A solution is prepared of diamine, dianhydride, and solvent. Aromatic dianhydrides are preferred because they give polyimides having better thermal properties. Examples of suitable aromatic dianhydrides include:
1,2,5,6-naphthalene tetracarboxylic dianhydride;
1,4,5,8-naphthalene tetracarboxylic dianhydride;
2,3,6,7-naphthalene tetracarboxylic dianhydride;
2-(3′, 4′-dicarboxyphenyl) 5,6-dicarboxybenzimidazole dianhydride;
2-(3′,4′-dicarboxyphenyl) 5,6-dicarboxybenzoxazole dianhydride;
2-(3′,4′-dicarboxyphenyl) 5,6-dicarboxybenzothiazole dianhydride;
2,2′,3,3′-benzophenone tetracarboxylic dianhydride;
2,3,3′,4′-benzophenone tetracarboxylic dianhydride;
3,3′,4,4′-benzophenone tetracarboxylic dianhydride (BTDA);
2,2′,3,3′-biphenyl tetracarboxylic dianhydride;
2,3,3′,4′-biphenyl tetracarboxylic dianhydride;
3,3′,4,4′-biphenyl tetracarboxylic dianhydride (BPDA);
bicyclo-[2,2,2]-octen-(7)-2,3,5,6-tetracarboxylic-2,3:5,6-dianhydride;
bis (3,4-dicarboxyphenyl) sulfone dianhydride;
bis (3,4-dicarboxyphenyl) sulfoxide dianhydride;
bis (3′4′-dicarboxyphenyl oxadiazole-1,3,4) paraphenylene dianhydride;
bis (3,4′-dicarboxyphenyl) 2,5-oxadiazole-1,3,4 dianhydride;
bis (3,4-dicarboxyphenyl) ether dianhydride or oxydiphthalic anhydride (ODPA);
bis (3,4-dicarboxyphenyl) thioether dianhydride; bisphenol A bisether dianhydride;
2,2′-bis (3,4-dicarboxyphenyl) hexafluoropropane dianhydride (6FDA); hydroquinone bisether dianhydride;
bis(3,4-dicarboxyphenyl) methane dianhydride;
cyclopentadienyl tetracarboxylic acid dianhydride;
cyclopentane tetracarboxylic dianhydride;
ethylene tetracarboxylic acid dianhydride;
perylene 3,4,9,10-tetracarboxylic dianhydride;
pyromellitic dianhydride (PMDA);
tetrahydrofuran tetracarboxylic dianhydride; and 5,5-[2,2,2-trifluoro-1-(trifluoromethyl)ethylidene]bis-1,3-isobenzofurandione).

The preferred dianhydrides, in order of increasing solubility of the resulting polyimides, are PMDA, BPDA, BTDA, ODPA, and 6FDA. Polyimides made from mixtures of dianhydrides tend to be more soluble than polyimides made from either dianhydride alone, and therefore mixtures of dianhydrides are preferred when increased solubility is desired.

Any solvent that will dissolve the polyamic acid, and preferably will also dissolve the polyimide, can be used in this invention. Examples of solvents that may be suitable include 2-vinyl pyrrolidone, acetone, Cellosolve acetate (hydroxyethyl acetate glycol mono-acetate), triethylamine (TEA), Cellosolve (glycol ethylether), diethylether, dichloromethane, dimethylformamide, dimethylacetamide (DMAC), ethyl alcohol, diglyme, triglyme, methylisobutylketone, methylethylketone, N-methyl pyrrolidone (NMP), sulfolane, toluene, and xylene. The preferred solvent is NMP because it solublizes more polyimides than the other solvents do and is believed to be of low toxicity. Sometimes the addition of a cosolvent is useful to provide a homogeneous solution. Toluene and tetrahydrofuran (THF) with NMP are examples of cosolvents. Sufficient solvent should be used to form a solution of about 10 to about 35 wt% solids. More or less solvent can be used to control the thickness of the film.

The solution may optionally contain a siloxane diamine and/or a diamine that is not crosslinkable, where the total amount of all diamines present is about stoichiometric with the amount of dianhydride used. Up to about 50 wt% of the total weight of diamines used can be siloxane diamine, and preferably the weight of siloxane diamine is about 5 to about 25 wt%. Siloxane diamine is preferably present to increase the solubility of the polyimide, reduce its water absorption, and give it better adhesion and lower dielectric constant. In general, the more siloxane diamine that is present, the more soluble will be the polyimide. A description of siloxane diamines that can be used in this invention can be found in U.S. Pat. No. 4,829,131, herein incorporated by reference. Useful siloxane diamines have the general formula

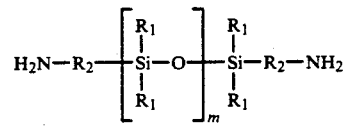

where each $R_1$ is independently selected from a substituted or unsubstituted aliphatic mono-radical with 1 to 12 carbon atoms or a substituted or unsubstituted aromatic mono-radical with 6 to 12 carbon atoms, and m, the number of repeated siloxane groups, can be 0 to 200 and is preferably 1 to about 12. (the term "Gm" is used to indicate a siloxane diamine of m repeated units.) Suitable $R_1$ groups include —$CH_3$, —$CF_3$, —$(CH_2)_5CF_3$, —$C_6H_5$, —CH=$CH_2$, —$CF_2$—CHF—$CF_3$, and

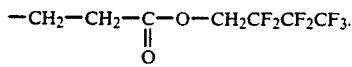

In the formula, $R_2$ has the same definition as $R_1$, but is a di-radical instead of a mono-radical. Examples of suitable $R_2$ groups include —$(CF_2)_s$—, —$(CH_2)_s$—, —$(CH_2)_s(CF_2)_t$—, —$C_6H_4$—, and —$(CH_2)_4$—O—$C_6H_4$— where s and t are each independently selected from 1 to 10. An example of a suitable siloxane diamine is $\alpha,\omega$-bis(3-aminopropyl)polydimethylsiloxane.

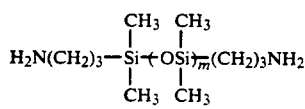

Examples of non-crosslinkable diamines that can be used in making the polyamic acid of this invention include 2,4-diaminotoluene, 2,5-diaminotoluene, 2,6-diaminotoluene, m-xylyldiamine, 2,4-diamine-5-chlorotoluene, 2,4-diamine-6-chlorotoluene, m-phenylenediamine, p-phenylenediamine, 2,2-bis(4-phenoxy aniline) isopropylidene, trifluoromethyl-2,4-diaminobenzene, trifluoromethyl-3,5-diaminobenzene, 4,4'-diamino-2,2'-trifluoromethyl diphenyloxide, 3,3'-diamino-5,5'-trifluoromethyl diphenyloxide, 4,4'-trifluoromethyl-2,2'-diamino biphenyl, 3,4'-oxydianiline, 4,4'-oxydianiline, 2,4,6-trimethyl-1,3-diaminobenzene, 2,2'-bis(4-aminophenyl)hexafluoropropane, m,m-methylene dianiline, m,m-sulfone dianiline, o,m-sulfone dianiline, and diaminoanthraquinone. Up to 40 wt % of the diamine used may be non-crosslinkable diamine. However, preferably the non-crosslinkable diamine is present in small amounts or is not used as it reduces the crosslinking density of the polyimide.

Up to 10 wt % of a chain stopper can also be added to control molecular weight. Chain stoppers are generally monofunctional anhydrides or primary amines. Examples of chain stoppers include allyl amine, phthalic anhydride, substituted phthalic anhydride, aniline, and substituted aniline.

The polyamic acid can be made at room temperature, preferably under nitrogen for about 4 to about 12 hours. The reaction is complete when the viscosity has increased, or the reaction can be followed by gel permeation chromatography.

The polyamic acid can have the repeating units

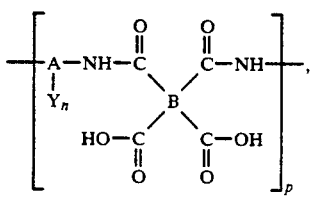

-continued

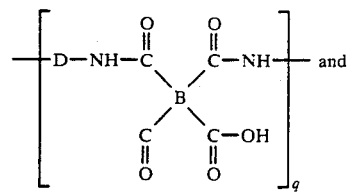

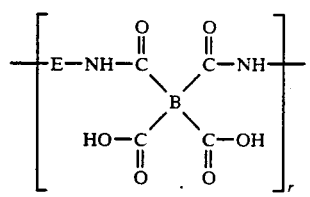

where A is a trivalent group containing at least one aromatic ring, each B is independently selected from a tetravalent group containing at least one aromatic ring, D is a siloxane-containing divalent group, E is a divalent group that does not contain pendant olefinic unsaturation, each Y is independently selected from the group consisting of

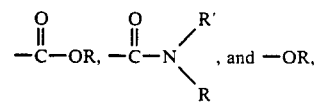

R is a group containing at least one olefinically unsaturated group, R' is hydrogen, alkyl to $C_{25}$, aryl, or R, n is 1 to 4, the number of olefinic groups in $Y_n$ is at least 3 when each Y is

and otherwise is at least 2, q is a number selected such that D is 0 to 50 wt % of $AY_n$, and r is a number selected such that E is 0 to 40 wt % of $AY_n$.

Polyamic Acid Coatings

Once a solution of the polyamic acid has been prepared, the solution can be used to form a polyamic acid coating on a substrate, or a polyimide can be prepared before a substrate is coated. Normally, a coating of the polyamic acid will be used only if the polyimide is insoluble. Preferably, however, a soluble polyimide is prepared to avoid the evolution of water from the coating when the imide ring is closed.

In order to make a crosslinkable polyamic acid coating, a polyamic acid coating solution is prepared. This solution typically contains about 10 to about 30 wt % of a crosslinkable polyamic acid according to this invention.

To facilitate the absorption of light, the polyamic acid coating solution also contains about 1 to about 10 wt %, based on total solids weight, of a sensitizer. In some instances the sensitizer not only absorbs the light, but also initiates the chemical reaction. Examples of suitable sensitizers include anthraquinone, 2-methylanthraquinone, 2-ethylanthraquinone, benzoquinone, 1,2-naphthoquinone, 1,4-naphthoquinone, 1,2-benzoanthraquinone, acetophenone, benzophenone, p,p'-diaminobenzophenone, p,p'-dimethylaminobenzophenone, p,p'-tetramethyldiaminobenzophenone (Micheler's ketone), isopropylthioxanthone, 2,2-dimethoxy-2-phenyl acetophenone, 2,-methyl-1-[4-(methylthio)phenyl]-2-morpholinopropane-1, 2-nitrofluorene, 5-nitroacenaphthene, 4-nitro-1-napthylamine, N-acetyl-4-nitro-1-napthylamine -p-nitroaniline, 2-chloro-4-nitroaniline, pycramide, 2-t-butylanthroquinone, 1,2-benzanthroquinone, anthrone, 1,9-benzoanthrone, 3-methyl-1,3-diaza-1,9-benzoanthrone, and dibenzalacetone. The preferred sensitizer is Michler's ketone which absorbs light at a wavelength of 365 nm because it gives a rapid cure. Optionally, photoinitiators can be used alone or in combination with photosensitizers.

With some polymers it may be useful to include about 0.1 to about 20 wt % (based on solids) of an optional crosslinking agent. The purpose of the crosslinking agent is to form a bridge between crosslinkable groups on different polymer chains and thereby promote crosslinking. In general, the crosslinking agent is a compound that has at least two pendant olefinic groups attached to an aromatic ring. Examples of suitable crosslinking agents are disclosed in Japanese patents 1,172,426 and 1,185,635. These agents have the general formula

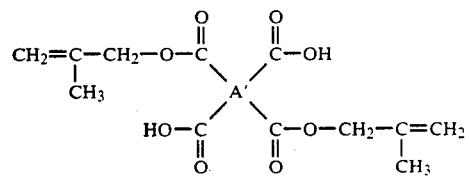

where A' is a group containing at least one aromatic ring such as

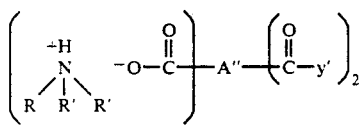

where G is $$-CH_2-, -S-, -O-, -\overset{O}{\underset{\|}{C}}-, -\overset{O}{\underset{\|}{\underset{\|}{S}}}-, \text{ or } -\overset{CH_3}{\underset{CH_3}{\underset{|}{C}}}-$$

and h is 0 or 1.

We have prepared crosslinking agents from dianhydrides that contain more than 4 olefinic groups and found them to be useful. These agents have the general formula $$\left( \begin{array}{c} {}^+H \\ N \\ R \quad R' \quad R' \end{array} -O-\overset{O}{\underset{\|}{C}}-A''-\left(\overset{O}{\underset{\|}{C}}-y'\right) \right)_2$$

where y' is —OR or

R and R' are as previously defined, and A'' is an aromatic or cycloaliphatic group.

Examples of these crosslinking agents are

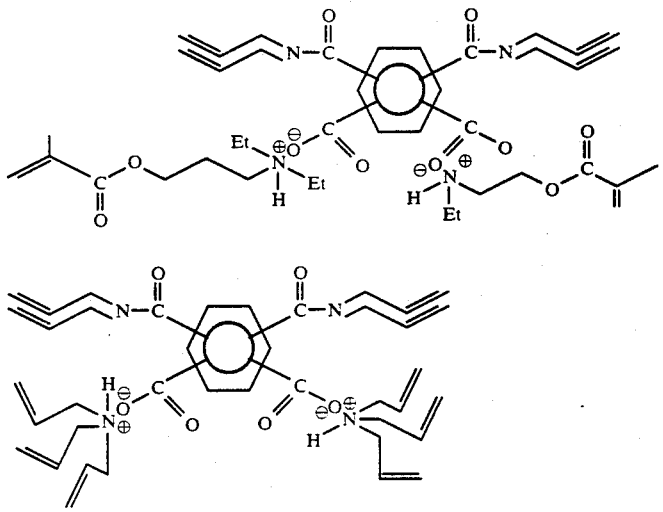

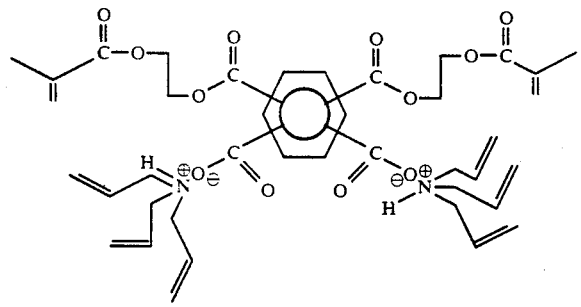

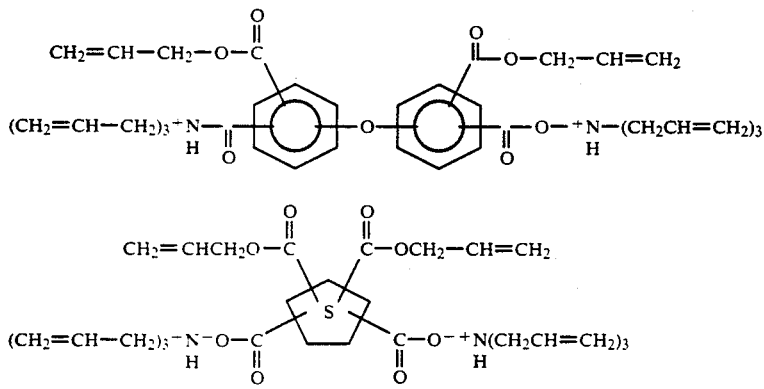

Other crosslinking agents known to the art, such as pentaerythrityl tetraacrylate, pentaerythrityl tetramethacrylate, ethylene glycol diacrylate, etc., can also be used.

A polyamic acid coating on a substrate can be made by spreading the coating solution on the substrate. Spreading can be accomplished by, for example, spin-coating, spraying, brushing, or other technique. Substrates can include plastic, glass, silicon, metals, ceramics, and semiconducting materials. The preferred substrate is a conducting or semiconducting material for use in preparing devices. After the substrate has been coated, it is heated to a temperature high enough to evaporate the solvent but not high enough to crosslink the polymer. If the solvent is NMP, that temperature is about 80° C. If a pattern on the coating is desired, this can be accomplished by masking the coating, exposing it to light of a wavelength that will activate the particular sensitizer selected, and dissolving and removing the uncrosslinked polyamic acid with a solvent. The remaining polyamic acid coating can then be imidized by heating at about 150° to about 300° C. for about 10 to about 100 minutes. The polyimide can have the repeating units

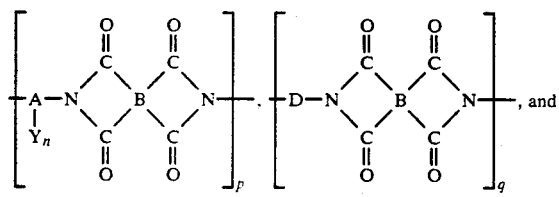

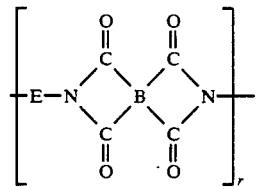

Polyimide Coatings

A polyimide coating can be made from a solution of the polyamic acid (without the presence of the sensitizer, initiator, or crosslinking agent) by heating the polyamic acid to a temperature of about 120° to about 200° C. for about 10 to about 200 minutes, which forms the corresponding polyimide. About 0.5 to about 2.5 wt %, based on solids, of a catalyst, such as a tertiary amine, can be used. Generally, about 10 wt % toluene is also used to remove water as a low boiling azeotrope. Other methods of solution imidization, such as reacting at room temperature in the presence of acetic anhydride and an amine, can also be used. The reaction is complete when the emission of water ceases. If the polyimide is insoluble, it will precipitate as it forms. However, if the polyimide is soluble, it will remain in solution after its imidization. The polyimide can be used as is or it can be isolated as a powder by precipitation in an antisolvent, such as water or methanol, then redissolved at the desired concentration. To the solution of the polyimide can be added the sensitizer, initiator, and optional crosslinking agent, as hereinabove described. The solution can then be coated onto a substrate by one of the techniques described for coating the polyamic acid. To form a pattern in the polyimide coating, the solvent is evaporated and a mask is placed over the polyimide layer and it is exposed to light, which crosslinks and insolublizes the exposed portions of the polyimide. The unexposed portions are then removed by dissolution in a solvent.

The following examples further illustrate this invention.

EXAMPLE 1

Preparation of Unsaturated Diamines

Purified pentaerythrityl triacrylate was reacted with 3,5-dinitrobenzoyl chloride in methylene chloride with triethylamine catalyst at about 20° to 25° C. The triethylamine hydrochloride that precipitated was filtered off and the methylene chloride was stripped off under vacuum to give the crude 3,5-dinitroester.

The nitro groups were reduced to amine groups with Fe powder and glacial acetic acid (approximately 10 moles per mole dinitro ester) and water at 25° C. The product was recovered by ethylacetate wash, then water and aqueous $NaHCO_3$ washing followed by stripping under vacuum. The crude pentaerythrityl triacrylate 3,5-diaminobenzoate was purified on a silica gel column with hexane/ethyl acetate eluent and characterized by nuclear magnetic resonance (NMR) and infrared (IR).

Similarly, the 3,5-diaminobenzoates of triallyl pentaerythrityl (TAP), pentaerythritol trimethacrylate (PETM), and the diallyl 3,5-diaminobenzamide were prepared. Table I gives the reactants and the diamines that were made.

TABLE I

| UNSATURATED DIAMINES | |
|---|---|
| Diamine Product | Unsaturated Reactant |
| PETA | Pentaerythrityl triacrylate |
| TAP | Triallylpentaerythritol |
| PETM | Pentaerythrityl trimethacrylate |
| DAA | Diallylamine |

EXAMPLE 2

Preparation and Testing of Polyamic Acids

A clean, dry 100 ml 3-necked flask equipped with a condenser with dry nitrogen flow on top (with pressure release), thermometer, and magnetic stirrer, was charged with 1.7667 gm TAP, 0.8975 gm $G_5$ $\alpha,\omega$-bis(3-aminopropyl)polydimethylsiloxane, MW=544 by titration), 10.7 ml dry NMP, and 1.2 ml toluene. To the solution was added 1.8185 gm BPDA and stirring was continued at room temperature for approximately 23 hours, forming the polyamic acid. This solution was very clear and moderately viscous.

To the solution was mixed a sensitizer that consisted of 6 wt % benzophenone-4 wt % Michler's ketone. The solution was spin coated on a silicon disc. The disc was exposed to a mercury arc lamp for 3 minutes through a mask and was developed 60 seconds in 1:6 volume ratio of triglyme:methylisobutyl ketone. It was finally rinsed with xylene and formed an excellent pattern useful in microelectronic applications. Table II gives the component monomers of the polyamic acids and the results.

TABLE II

| | POLYAMIC ACIDS | | | |
|---|---|---|---|---|
| Example | Dianhydride (gm) | Siloxane (gm) | Diamine (gm) | Pattern Formed |
| 2a | BPDA 1.8185 | $G_5$ 0.8975 | TAP 1.7667 | Yes |
| 2b | BPDA 1.7470 | $G_5$ 0.2916 | PETM 2.6971 | Yes |
| 2c | BPDA 1.3636 | — | PETA 2.0024 | Yes |
| 2d | BPDA 1.3671 | — | TAP 1.8123 | Yes |
| 2e | BPDA 2.2923 | — | DAA 1.7999 | Yes |
| 2f | BPDA 2.4160 | $G_5$ 0.2262 | DAA 1.8009 | Yes |
| 2g | BPDA 2.5648 | $G_5$ 0.4994 | DAA 1.8015 | Yes |

Note: 1.5 hour reaction time. 15 ml NMP

EXAMPLE 3

Preparation and Testing of Imidized Polymers

This example illustrates a coating formed from soluble polyimides. Generally, polyamic acids having pendant allyl groups were imidized at 170° C. with 1.5 wt % (based on the weight of solids in the charge) of diazabicyclooctane sold by Aldrich Chemical Co. under the trademark "Dabco" and toluene to form an azeotrope, as in Example 1. The less stable polyamic acids having pendant acrylic and methacrylic groups were imidized at room temperature with acetic anhydride and triethylamine.

Generally the diamines (unsaturated and $\alpha,\omega$-bis(3-aminopropyl)polydimethylsiloxane) were charged to a small (100 cc typically) 3-necked flask equipped with condenser with nitrogen inlet on top, thermometer, and magnetic stirrer. Dry NMP was added and the diamines were dissolved. Toluene (10 vol % based on the NMP) was added. Then the anhydrides were added and the mixture was stirred under nitrogen for about 16 hours to form the polyamic acid.

Imidization of the polyamic acid was performed either method A or method B:

A) at 170° C. with a Dean Stark trap and toluene and 1.5 wt %, based on solids, or Dabco for approximately two hours, or B) at room temperature with TEA (approximately 1.14×moles dianhydride) and acetic anhydride ($Ac_2O$) (approximately 11×moles dianhydride) for about 16 hours.

The products were recovered by precipitation into a small blender with methanol. Then they were suction filtered and dried under vacuum.

Table III gives the polymers prepared and the method of preparation. NMP solutions (generally with a photoinitiator system) were prepared from each material. These were spin coated on small silicone wafers, exposed to light (UV to visable) and developed (with, for example, mixtures of diglyme or triglyme and methylisobutylketone).

Percent Imidization

The imidized polymers were dissolved in NMP and were titrated with tetrabutylammonium hydroxide. This value was used to calculate % imidization.

TABLE III

| | PREPARATION OF IMIDIZED MATERIALS | | | | | | | |
|---|---|---|---|---|---|---|---|---|
| Example | Crosslinkable Diamine (gm) | Siloxane Diamine (gm) | Dianhydride (gm) | NMP (ml) | Toluene (ml) | Imidization Method | Percent Imidization | Pattern Formed |
| 3a | TAP 1.8664 | G₅ 0.9141 | ODPA 2.0050 | 10.7 | 1.2 | B | 94 | Yes |
| 3b | TAP 1.8602 | G₅ 0.9189 | ODPA 2.0028 | 10.7 | 1.2 | A | 96 | Yes |
| 3c | TAP 2.8029 | — | ODPA 2.2279 | 11.7 | 1.2 | A | 100 | Yes |
| 3d | PETM 2.003 | G₅ 0.9183 | ODPA 1.8341 | 11.1 | 1.2 | B | 91 | Yes |
| 3e | TAP 2.2807 | — | 6FDA 2.2789 | 9.9 | 0.9 | A | 93 | Yes |
| 3f | TAP 1.8142 | G₅ 0.2138 | ODPA 1.5640 | 9.0 | 0.8 | B | 92 | Yes |
| 3g | TAP 1.9925 | G₁ 0.1998 | ODPA 1.8335 | 10.0 | 1.0 | B | 88 | Yes |
| 3h | TAP 2.0014 | G₁₂ 0.2046 | ODPA 1.6493 | 10.0 | 1.0 | B | 90 | Yes |
| 3i | TAP 1.8765 | G₅ 0.2329 | ODPA/BTDA 1/1 0.8132/0.8476 | 9.0 | 0.9 | B | 92 | Yes |
| 3j | Ethyl[1] 1.7903 | G₅ 0.2107 | ODPA 3.2037 | 12.1 | 1.2 | B | Not Soluble | |
| 3k | TAP 1.8720 | G₁₅[2] 0.9280 | ODPA 1.9437 | 11.1 | 1.2 | B | 97 | Yes |
| 3l | DAA 1.7999 | G₅ 0.2318 | ODPA 2.5477 | 18.2 | 1.8 | A | Not Soluble | |
| 3m | TAP 1.855 | G₅ 0.2209 | ODPA 1.6013 | 9.0 | 1.0 | A | 94 | Yes |
| 3n | PETM 2.0101 | G₅ 0.1872 | ODPA 1.4215 | 8.6 | 0.9 | B | 92 | Yes |
| 3o | PETM 1.9916 | G₅ 0.1850 | ODPA/6FDA 1/1 0.7040/1.0083 | 19.8 | 2.0 | B | — | Yes |
| 3p | DAA 1.7957 | G₅ 0.2369 | ODPA/6FDA 1/1 1.2725/1.8226 | 18.2 | 1.8 | A | — | Yes |
| 3q* | Ethyl[1] 1.7997 | G₅ 0.2370 | ODPA/6FDA 1/1 1.2752/1.8264 | 20.6 | 2.0 | A | — | No |
| 3r | PETM 1.9901 | G₅ 0.2010 | ODPA/6FDA 3/1 1.0624/0.5071 | 20.0 | — | B | — | Yes |

[1] Ethyl 3,5-diaminobenzoate - used for comparison, not part of invention
[2] bisaminopropylpolymethylvinylsiloxane

We claim:

1. An aromatic crosslinkable diamine having the general formula

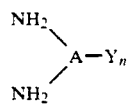

where A is a group containing at least one aromatic ring, each Y is independently selected from the group consisting of

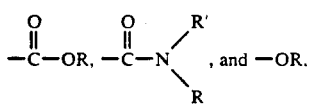

R is a group containing at least one olefinically unsaturated group, R' is hydrogen, alkyl to $C_{25}$, aryl, or R, n is 1 to 4, and the number of olefinic groups in each Y is at least 3 when each Y is

and otherwise is at least 2.

2. A diamine according to claim 1 wherein A is

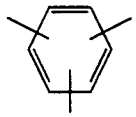

3. A diamine according to claim 1 wherein Y is

4. A diamine according to claim 1 wherein Y is

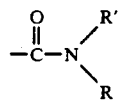

5. A diamine according to claim 1 wherein R is a radical formed from triallyl pentaerythritol, pentaerythrityl trimethacrylate, pentaerythrityl triacrylate, dipentaerythrityl pentaacrylate, dipentaerythrityl pentamethacrylate, and mixtures thereof.

6. A diamine according to claim 1 wherein said diamine is selected from the group consisting of triallylpentaerythrityl-3,5-diaminobenzoate, pentaerythrityl trimethyacrylate-3,5-diaminobenzoate, pentaerythrityl triacrylate-3,5-diaminobenzoate, and N,N-diallyl-3,5-diaminobenzamide.

7. A method of making a diamine according to claim 1 wherein Y is $$-\overset{O}{\underset{\|}{C}}-OR \text{ or } -\overset{O}{\underset{\|}{C}}-N\overset{R'}{\underset{R}{\diagdown}}$$

comprising reacting a dinitro acid chloride with an unsaturated alcohol or an unsaturated amine, and reducing the nitro groups to amine groups.

8. A method of making a polyamic acid comprising reacting a diamine according to claim 1 with a dianhydride.

9. A polyamic acid having the repeating units $$\left[ \begin{array}{c} A-NH-\overset{O}{\underset{\|}{C}} \diagup \overset{O}{\underset{\|}{C}}-NH \\ | \\ Y_n \\ HO-\underset{\|}{C} \diagdown B \diagup \underset{\|}{C}-OH \\ O \quad O \end{array} \right]_p ,$$

$$\left[ \begin{array}{c} D-NH-\overset{O}{\underset{\|}{C}} \diagup \overset{O}{\underset{\|}{C}}-NH \\ \underset{\|}{C} \diagdown B \diagup \underset{\|}{C}-OH \\ O \quad O \end{array} \right]_q \text{ and }$$

$$\left[ \begin{array}{c} E-NH-\overset{O}{\underset{\|}{C}} \diagup \overset{O}{\underset{\|}{C}}-NH \\ HO-\underset{\|}{C} \diagdown B \diagup \underset{\|}{C}-OH \\ O \quad O \end{array} \right]_r$$

where A is a trivalent group containing at least one aromatic ring, each B is independently selected from a tetravalent group containing at least one aromatic ring, D is a siloxane-containing divalent group, E is a divalent group that does not contain pendant olefinic unsaturation, each Y is independently selected from the group consisting of $$-\overset{O}{\underset{\|}{C}}-OR, \; -\overset{O}{\underset{\|}{C}}-N\overset{R'}{\underset{R}{\diagdown}}, \text{ and } -OR$$

R is a group containing at least one olefinically unsaturated group, R' is hydrogen, alkyl to $C_{25}$, aryl, or R, n is 1 to 4, the number of olefinic groups in $Y_n$ is at least 3 when each Y is $$-\overset{O}{\underset{\|}{C}}-OR$$

and otherwise is at least 2, q is a number selected such that D is 0 to 50 wt % of AYn, and r is a number selected such that E is 0 to 40 wt % of AYn.

10. A polyamic acid according to claim 9 wherein B is selected from the group consisting of

[structures shown]

, and

[structure shown]

11. A polyamic acid according to claim 9 wherein D is 5 to 25 wt % of AYn.

12. A method of forming a polyimide comprising heating a polyamic acid according to claim 9 to a temperature sufficient for imidization to occur.

13. A solution comprising
(A) a polyamic acid according to claim 9;
(B) about 1 to about 10 wt %, based on polyamic acid weight, of a sensitizer;
(C) about 0.1 to about 20 wt %, based on polyamic acid weight, of a crosslinking agent; and
(D) about 70 to about 90 wt % solvent.

14. A solution according to claim 13 wherein said crosslinking agent has the formula $$CH_2=\underset{CH_3}{\overset{|}{C}}-CH_2-O-\overset{O}{\underset{\|}{C}} \diagup \overset{O}{\underset{\|}{C}}-OH \\ HO-\underset{\|}{C} \diagdown A' \diagup \underset{\|}{C}-O-CH_2-\underset{CH_3}{\overset{|}{C}}=CH_2 \\ O \quad O$$

where A' is a group containing at least one aromatic ring.

15. A solution according to claim 13 wherein said crosslinking agent has the formula $$\left( \underset{R \; R' \; R'}{\overset{+H}{\underset{|}{N}}} -O-\overset{O}{\underset{\|}{C}} \right)- A'' \left( \overset{O}{\underset{\|}{C}}-y' \right)_2$$

where y' is —OR or $$-N\overset{R}{\underset{R'}{\diagdown}} ,$$

R is a group containing at least one olefinically unsaturated group, R' is hydrogen, alkyl to $C_{25}$, aryl, or R, and A" is an aromatic or cycloaliphatic group.

16. A method of forming a polyimide coating on a substrate comprising spreading a solution according to claim 13 on said substrate, evaporating said solvent, exposing at least some of said polyamic acid to light to crosslink and insolublize polyamic acid exposed to said light, solublizing and removing polyamic acid that was not exposed to said light, and heating polyamic acid remaining on said substrate to form said polyimide coating.

17. A method according to claim 16 wherein said substrate is a semiconducting material.

18. A polyimide having the repeating units

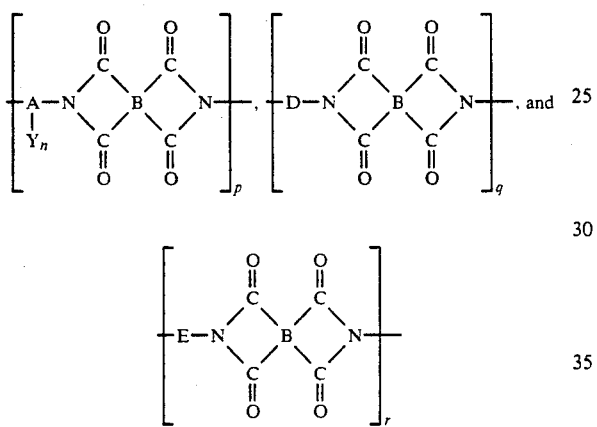

where A is a trivalent group containing at least one aromatic ring, B is a tetravalent group containing at least one aromatic ring, D is a siloxane-containing divalent group, E is a divalent group that does not contain pendant olefinic unsaturation, each Y is independently selected from the group consisting of

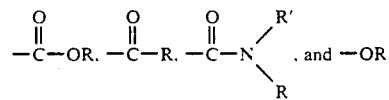

R is a group containing at least one olefinically unsaturated group, R' is hydrogen, alkyl to $C_{25}$, aryl, or R, n is 1 to 4, the number of olefinic groups in Y is at least 3 when each Y is

and otherwise is at least 2, q is a number selected such that D is 0 to 50 wt % of AYn, and r is a number selected such that E is 0 to 40 wt % of AYn.

19. A polyimide according to claim 18 which is soluble.

20. A solution comprising
(A) a polyimide according to claim 19;
(B) about 1 to about 10 wt %, based on polyimide weight, of a sensitizer;
(C) about 0.1 to about 20 wt %, based on polyimide weight, of a crosslinking agent; and
(D) about 70 to about 90 wt % solvent.

21. A method of forming a polyimide coating on a substrate comprising spreading a solution according to claim 20 on said substrate, evaporating said solvent, exposing at least some of said polyimide to light to crosslink and insolublize polyimide exposed to said light, and solublizing and removing polyimide that was not exposed to said light.

22. A method according to claim 21 wherein said substrate is a semiconducting material.

23. A semiconducting chip comprising a silicon substrate having a coating of a polyimide according to claim 18 thereon.

24. A semiconducting chip according to claim 23 wherein said polyimide coating is in a circuit pattern.

25. A semiconducting chip according to claim 23 wherein said polyimide has been crosslinked.

26. A semiconducting chip according to claim 25 wherein said polyimide coating is in a circuit pattern.

* * * * *